(12) United States Patent
Hauer et al.

(10) Patent No.: US 7,531,331 B2
(45) Date of Patent: May 12, 2009

(54) BUTYNOL I ESTERASE

(75) Inventors: Bernhard Hauer, Fußgönheim (DE);
Thomas Friedrich, Darmstadt (DE);
Christoph Nübling, Haßloch (DE);
Rainer Stürmer, Ródersheim-Gronau (DE); Wolfgang Ladner, Fußgönheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 379 days.

(21) Appl. No.: 10/362,530

(22) PCT Filed: Aug. 30, 2001

(86) PCT No.: PCT/EP01/10040

§ 371 (c)(1),
(2), (4) Date: Feb. 25, 2003

(87) PCT Pub. No.: WO02/18560

PCT Pub. Date: Mar. 7, 2002

(65) Prior Publication Data

US 2005/0181472 A1     Aug. 18, 2005

(30) Foreign Application Priority Data

Aug. 31, 2000   (DE) ................. 100 42 892
Jun. 29, 2001   (DE) ................. 101 31 544

(51) Int. Cl.
*C12P 7/62*     (2006.01)
*C12P 7/64*     (2006.01)
*C12P 21/06*    (2006.01)
*C12N 9/18*     (2006.01)

(52) U.S. Cl. .............. 435/135; 435/134; 435/197

(58) Field of Classification Search ................... None
See application file for complete search history.

(56) References Cited

OTHER PUBLICATIONS

Nakamura et al., *Tetrahedron:Asymmetry*, 9 (1998) 4429-4439.
Yang et al. *J.Org.Chem.*, 64 (1999) 1709-12.
Balkenhohl et al., *J.Prakt.Chem.*, 339 (1997) 381-384.
Manco et al., *Biochem.J.*, 332 (1998) 203-212.
Faraldos et al., *Synlett*, Apr. 1997, 367-370.
Khalameyzer et al., *App.&Env.Microbiol.*, 65:2 (Feb. 1999) 477-482.
Peist et al., *J. Bacteriology*, 179:24 (1997), 7679-7686.
Gudelj et al., *J.Mol.Cat.B:enzymatic*, 5 (1998) 261-266.
Pearson et al., *Proc.Natl.Acad.Sci.USA*, 85 (Apr. 1998) 2444-2448.
Narang, Saran, *Tetrahedron*, 39:1 (1983) 3-22.
Itakura et al. *Ann.Rev.Biochem.*, 53 (1984) 323-56.
Itakura et al., *Science*, 198 (Dec. 1977) 1056-1063.
Arkin et al,. *Proc.Natl.Acad.Sci.USA*, 89 (Aug. 1992) 7811-7815.
Ike et al., *Nucleic Acids Research*, 11:2 (1983) 477-488.
Delagrave et al., *Protein Eng.*, 6:3 (1993) 327-331.

*Primary Examiner*—Nashaat T Nashed
*Assistant Examiner*—Mohammad Younus Meah
(74) *Attorney, Agent, or Firm*—Novak Druce + Quigg LLP

(57) ABSTRACT

The invention relates to novel proteins from *Pseudomonas glumae*, having esterase activity, in particular butynol I esterase activity, to nucleic acid sequences coding therefor, to expression cassettes, vectors and recombinant microorganisms; to methods for preparing said proteins and to the use thereof for enzymic, in particular enantioselective enzymic, ester hydrolysis or transesterification of organic esters.

16 Claims, 1 Drawing Sheet

Fig. 1

```
Query:  1420 IVVALYAVLFAFTLFTAHQVRRRFPPEGKFVEIDGDRLHYVDYGSGPPIVMVHGLCGQLL 1599
             ++V   V +  ++   ++    P G+FVE+DG+R HY + G GPP+VM+HGL G
Sbjct:    11 VLVGASVVFWGLSAWMTRRIEAAVPGNGRFVEVDGERFHYYEEGKGPPLVMIHGLMGSSR 70

Query:  1600 NFAYLDLARLAQSHRVILVDRAGSGRSTRGPASRANVYAQARGIARFIETLGLERPVLVG 1779
             N Y   +L +  RVI +DR GSG STR   + A++ AQAR +A FI  LGL++P+++G
Sbjct:    71 NLTYALSRQLREHFRVITLDRPGSGYSTRHKGTAADLPAQARQVAAFINQLGLDKPLVLG 130

Query:  1780 HSLGGAIALAVGLDYPERVSRIALIAPLTHTETEPPKXXXXXXXXXXXXXXXXXXTMGIP 1959
             HSLGGAI+LA+ LD+PE VS + L+APLTH +  P                   T+ +P
Sbjct:   131 HSLGGAISLALALDHPEAVSGLVLVAPLTHPQPRLPLVFWSLAVRPAWLRRFVANTLTVP 190

Query:  1960 IMILQSRKAIDAIFAPEPVPRDFPLKGGGMMGLRPEAFYAASSDLVAAPEDLPDMERRYP 2139
             + +L R  +  +FAP+ P DF +GGG++G+RP+ FYAASS++     + LP M +RYP
Sbjct:   191 MGLLTRRSVVKGVFAPDAAPEDFATRGGGLLGMRPDNFYAASSEIALVNDCLPGMVKRYP 250

Query:  2140 TLGVPVSMLYGRQDAILDFHKHGEGLKRKLDGVELSAVEG-GHMLPVT 2280
             L +P+ ++YG QD +LDF +HG+ L  K+ G++L  VEG GHMLP+T
Sbjct:   251 QLALPIGLIYGAQDKVLDFRRHGQALADKVPGLKLQVVEGRGHMLPIT 298
``` ns; to methods for preparing said proteins and to the use thereof for enzymic, in particular enantioselective enzymic, ester hydrolysis or transesterification of organic esters.
BUTYNOL I ESTERASE

FIELD OF THE INVENTION

The invention relates to novel proteins from *Pseudomonas glumae*, having esterase activity, in particular butynol I esterase activity, to nucleic acid sequences coding therefor, to expression cassettes, vectors and recombinant microorganisms; to methods for preparing said proteins and to the use thereof for enzymic, in particular enantioselective enzymic, ester hydrolysis or transesterification of organic esters.

BACKGROUND OF THE INVENTION

Esterases and lipases are hydrolases which can be employed in industrial processes for synthesizing optically active organic compounds and which are characterized by high substrate specificity. Through a mechanism similar to that of serine proteases, they can transfer acyl groups onto nucleophiles such as, for example, carbonyl groups or hydrolytically cleave ester bonds. Esterases, lipases and serine proteases share the catalytic triad, a sequence motif consisting of the amino acids Ser, His and Asp, where the carbonyl carbon atom is subject to nucleophilic attack by the active Ser, which, with participation of the other two amino acids, leads to a charge distribution. Esterases and lipases may also transfer acyl groups onto other nucleophiles, such as thioether thio groups or activated amines.

Lipases hydrolyze long-chain glycerol esters and are characterized by surface activation, i.e. the active site becomes accessible only in the presence of the lipid substrate. Lipases are stable in nonaqueous organic solvents and are employed in numerous industrial processes for kinetic racemate resolution, i.e. one enantiomer is converted substantially faster than the other. Said enantiomer can be subsequently obtained from the reaction solution owing to different physical and chemical properties.

Nakamura (Nakamura, K. et al., Tetrahedron; Asymmetry 9, (1999), 4429-4439) describes the racemate resolution of 1-alkyn-3-ol by transesterification in hydrophobic solvents with the aid of commercially available lipases (Amano AK, AH and PS; Amano Pharmaceuticals Co. Ltd.). In this reaction, enantioselectivity increases with the chain length of the acyl donor and sterically large residues (chloroacetate, vinylbenzoate) have an adverse effect on the reaction. Yang (Yang, H. et al., J. Org. Chem. 64, (1999), 1709-1712) describes the enantioselective preparation of optically active acids by transesterification with vinyl esters using lipase B from *Candida antarctica* as catalyst. In this case, ethyl esters lead to a distinctly lower reaction rate and selectivity. A lipase isolated from *Burkholderia plantarii* (*Pseudomonas plantarii* or *glumae*) DSM 6535 is employed for enantioselective acylation of racemic amines with the aid of ethyl methoxy-acetate (Balkenhohl, F. et al., J. prakt. Chem. 339, (1997), 381-384).

Esterases enantioselectively catalyze the formation and breaking of ester bonds (forward and reverse reaction). Preference is given to using vinyl esters in the transesterification for obtaining optically active alcohols, since the alcohol function of the ester is no longer available after the conversion due to tautomerization to the aldehyde or ketone and thus the reverse reaction can be avoided. In contrast to lipases, esterases are not surface-activated and also convert organic compounds of relatively short chain length. Esterases of different substrate specificity have been isolated from various organisms.

Thus the esterase from *Pseudocardia thermophila* FERM-BP-6275 is used for hydrolyzing optically active chromanacetic esters (EP-A-0 892 044).

An esterase from *Bacillus acidocaldarius* hydrolyzes with low enantioselectivity esters from a narrow range of substrates (Manco, G. et al., Biochem. J. 332, (1998), 203-212).

Acylase 1 from *Aspergillus* is used for obtaining secondary alcohols by transesterification with vinyl esters in organic nonpolar solvents, it being preferred to convert secondary alcohols having short side chains (Faraldos, J. et al., Synlett 4, (1997), 367-370). From *Pseudomonas fluorescens* DSM 50 106 a membrane-bound lactone-specific esterase has been cloned (Khalameyzer, V. et al., Appl. and Environ. Microbiol. 65(2), (1999), 477-482), and from the *E. coli* malQ mutant an acetylesterase has been cloned (Peist, R. et al., J. Bacteriol. 179, (1997), 7679-7686). However, enantioselectivity and substrate specificity of these two esterases have not been studied in more detail. *Rhodococcus* sp. NCBM 11216 expresses 4 esterases, RR1 to RR4, which have different specificity. For the ester synthesis from naphthol and an acid, RR1 and RR2 prefer acids with short carbon chains, while RR3 and RR4 specifically convert acids having relatively long carbon chains and sterically relatively large residues (Gudelj, M. et al., J. Mol. Cat. B, Enzymatic 5, (1998), 261-266).

However, esterases which have a wide range of substrates and a high enantioselectivity and which can be employed in industrial processes are not available for preparing small organic molecules, such as optically active alcohols, acids or esters with short carbon chains.

SUMMARY OF THE INVENTION

It is an object of the present invention to provide esterases which have at least one of the abovementioned properties.

We have found that this object is achieved, surprisingly, by providing a protein having butynol I esterase activity, which includes at least one amino acid part sequence according to SEQ ID NO: 3, 4, 5 or 6:

a) FIETLGLERPVLVGHSLGGAIALAVGLDYPER (SEQ ID NO:3), b) IALIAPLTHTETEP (SEQ ID NO:4), c) GGGMMGLRPEAFYAASSDLV (SEQ ID NO:5)

d) AIDAIFAPEPV (SEQ ID NO:6)

(each one given in the amino acid one-letter code, the first amino acid in each case corresponding to the respective amino-terminal end), and also the functional equivalents thereof having butynol I esterase activity.

BRIEF DESCRIPTION OF THE DRAWING

The invention is pointed out with particularity in the claims. The above and further advantages of this invention may be better understood by referring to the following description taken in conjunction with the accompanying drawing, in which:

FIG. 1 depicts a sequence alignment of an inventive amino acid part sequence of butynol I esterase with a part sequence of a lactone-specific esterase from *Pseudomonas fluorescens*. Query: part sequence of the clone LU2898 of the invention (SEQ ID NO: 7). Sbjct: part sequence of the *P. fluorescens* enzyme (Accession No.: 087637) (SEQ ID NO: 8).

DESCRIPTION OF THE INVENTION

The object was achieved in particular by providing a butynol I esterase which comprises an amino acid sequence according to SEQ ID NO:2 or is encoded by a nucleic acid sequence according to SEQ ID NO: 1 and also functional equivalents of said protein.

For the sake of simplicity, the abovementioned proteins are denoted butynol I esterases hereinbelow.

"Functional equivalents" or analogs of the specifically disclosed polypeptides or proteins are for the purposes of the present invention polypeptides or proteins which differ therefrom but which still have the desired biological activity, in particular enzymic activity.

"Functional equivalents" mean according to the invention in particular mutants which have in at least one of the abovementioned sequence positions an amino acid which differs from that specifically mentioned but nevertheless has at least one of the biological activities of the invention. "Functional equivalents" thus comprise the mutants available by one or more amino acid additions, substituents, deletions and/or inversions, it being possible for said modifications to occur in any sequence position as long as they lead to a mutant having the profile of properties of the invention. Functional equivalence exists in particular also when there is qualitative agreement between mutant and unmodified polypeptide in the reactivity pattern, i.e. there are differences in the rate of conversion of identical substrates, for example.

"Functional equivalents" naturally also comprise polypeptides which are obtainable from other organisms, and naturally occurring variants. For example homologous sequence regions can be found by sequence comparison, and equivalent enzymes can be established on the basis of the specific requirements of the invention.

"Functional equivalents" likewise comprise fragments, preferably single domains or sequence motifs, of the polypeptides of the invention, which have, for example, the desired biological function.

"Functional equivalents" are additionally fusion proteins which have one of the abovementioned polypeptide sequences or functional equivalents derived therefrom and at least one other heterologous sequence functionally different therefrom in functional N- or C-terminal linkage (i.e. with negligible mutual impairment of the functions of parts of the fusion proteins). Nonlimiting examples of such heterologous sequences are, for example, signal peptides, enzymes, immunoglobulins, surface antigens, receptors or receptor ligands.

"Functional equivalents" include according to the invention homologs of the specifically disclosed polypeptides or proteins. These have at least 60%, preferably at least 75%, in particular at least 85%, such as, for example, 90%, 95% or 99%, homology to one of the specifically disclosed sequences, calculated by the algorithm of Pearson und Lipman, Proc. Natl. Acad, Sci. (USA) 85(8), 1988, 2444-2448.

Homologs of the proteins or polypeptides of the invention can be generated by mutagenesis, for example by point mutation or truncation of the protein. The term "homolog" as used here relates to a variant form of the protein which acts as agonist or antagonist of the protein activity.

Homologs of the proteins of the invention can be identified by screening combinatorial libraries of mutants such as, for example, truncation mutants. It is possible, for example, to generate a variegated library of protein variants by combinatorial mutagenesis at the nucleic acid level, such as, for example, by enzymatic ligation of a mixture of synthetic oligonucleotides. There is a large number of methods which can be used to produce libraries of potential homologs from a degenerate oligonucleotide sequence. Chemical synthesis of a degenerate gene sequence can be carried out in an automatic DNA synthesizer, and the synthetic gene can then be ligated into a suitable expression vector. The use of a degenerate set of genes makes it possible to provide all sequences which encode the desired set of potential protein sequences in one mixture. Methods for synthesizing degenerate oligonucleotides are known to the skilled worker (for example Narang, S. A. (1983) Tetrahedron 39:3; Itakura et al. (1984) Annu. Rev. Biochem. 53:323; Itakura et al., (1984) Science 198: 1056; Ike et al. (1983) Nucleic Acids Res. 11:477).

In addition, libraries of fragments of the protein codon can be used to generate a variegated population of protein fragments for screening and for subsequent selection of homologs of a protein of the invention. In one embodiment, a library of coding sequence fragments can be generated by treating a double-stranded PCR fragment of a coding sequence with a nuclease under conditions under which nicking takes place only about once per molecule, denaturing the double-stranded DNA, renaturing the DNA to form double-stranded DNA, which may comprise sense/antisense pairs of different nicked products, removing single-stranded sections from newly formed duplices by treatment with S1 nuclease and ligating the resulting fragment library into an expression vector. It is possible by this method to derive an expression library which encodes N-terminal, C-terminal and internal fragments having different sizes of the protein of the invention.

Several techniques are known in the prior art for screening gene products from combinatorial libraries which have been produced by point mutations or truncation and for screening cDNA libraries for gene products with a selected property. These techniques can be adapted to rapid screening of gene libraries which have been generated by combinatorial mutagenesis of homologs of the invention. The most frequently used techniques for screening large gene libraries undergoing high-throughput analysis comprises the cloning of the gene library into replicable expression vectors, transformation of suitable cells with the resulting vector library and expression of the combinatorial genes under conditions under which detection of the required activity facilitates isolation of the vector which encodes the gene whose product has been detected. Recursive ensemble mutagenesis (REM), a technique which increases the frequency of functional mutants in the libraries, can be used in combination with the screening tests for identifying homologs (Arkin and Yourvan (1992) PNAS 89:7811-7815; Delgrave et al. (1993) Protein Engineering 6(3):327-331).

Preferred functional equivalents of the invention have a sequence deviating from SEQ ID NO: 2 in at least one position, and preferably said alteration in the sequence changes the esterase activity only insignificantly, i.e. by not more than approximately ±90, in particular ±50% or not more than ±30%. This change can be determined using a reference substrate such as, for example, butynol butyrate under standardized conditions (such as, for example, 20 mM substrate, 10 mM phosphate buffer, pH 7.4, T=20° C.).

The invention relates in particular to those functional equivalents which include at least one part sequence of at least 10 successive amino acids from the sequence according to SEQ ID NO: 2 and which have the above activity for the reference substrate.

Nonlimiting examples of part sequences of this kind are derived from the abovementioned part sequences according to SEQ ID NO: 3, 4, 5 and 6.

Furthermore preferred functional equivalents of the esterases of the invention thus include, for example, at least one part sequence derived from SEQ ID NO: 3, 4, 5 or 6, with, in comparison with the specifically stated part sequence, one or more amino acids having been substituted, deleted, inverted or added and with the esterase activity differing from the esterase activity of the native protein (SEQ ID NO:2) by not more than ±90% or ±50%, preferably by not more than ±30%.

The butynol I esterases of the invention preferably have a molecular weight of about 40 to 42 kDa, in particular about 41.3 kDa, determined by SDS gel electrophoresis. They are obtainable in particular from *Pseudomonas glumae* Lu 2023 with deposition number DSM 13176. Further strain variants are accessible, for example starting from *Pseudomonas glumae* Lu 8093, by selection such as, for example, culturing on minimal medium plates with ethyl phenylacetate as the sole carbon source.

The invention also includes polynucleotides coding for butynol I esterase and include a nucleic acid sequence according to SEQ ID NO:1 or a sequence derived therefrom.

The invention relates in particular to nucleic acid sequences (single- and double-stranded DNA and RNA sequences such as, for example, cDNA and mRNA), coding for one of the above polypeptides or proteins and their functional equivalents which are obtainable, for example, by use of artificial nucleotide analogs.

The invention relates both to isolated nucleic acid molecules which code for polypeptides or proteins of the invention or biologically active sections thereof, and to nucleic acid fragments which can be used, for example, for use as hybridization probes or primers for identifying or amplifying coding nucleic acids of the invention.

The nucleic acid molecules of the invention may additionally comprise untranslated sequences from the 3' and/or 5' end of the coding region of the gene.

An "isolated" nucleic acid molecule is separated from other nucleic acid molecules which are present in the natural source of the nucleic acid and may moreover be essentially free of other cellular material or culture medium if it is produced by recombinant techniques, or free of chemical precursors or other chemicals if it is chemically synthesized.

A nucleic acid molecule of the invention can be isolated by using standard techniques of molecular biology and the sequence information provided according to the invention. For example, cDNA can be isolated from a suitable cDNA library using one of the specifically disclosed complete sequences or a section thereof as hybridization probe and standard hybridization techniques (as described, for example, in Sambrook, J., Fritsch, E. F. und Maniatis, T. Molecular Cloning: A Laboratory Manual. 2nd edition, Cold Spring Harbor Laboratory, Cold Spring Harbor Laboratory Press, Cold Spring Harbor, N.Y., 1989). It is moreover possible for a nucleic acid molecule comprising one of the disclosed sequences or a section thereof to be isolated by polymerase chain reaction using the oligonucleotide primers constructed on the basis of this sequence. The nucleic acid amplified in this way can be cloned to a suitable vector and be characterized by DNA sequence analysis. The oligonucleotides of the invention can also be produced by standard synthetic methods, for example using an automatic DNA synthesizer.

The invention additionally comprises the nucleic acid molecules which are complementary to the specifically described nucleotide sequences, or a section thereof.

The nucleotide sequences of the invention make it possible to generate probes and primers which can be used for identifying and/or cloning homologous sequences in other cell types and organisms. Such probes and primers usually comprise a nucleotide sequence region which hybridizes under stringent conditions onto at least about 12, preferably at least about 25, such as, for example, 40, 50 or 75, consecutive nucleotides of a sense strand of a nucleic acid sequence of the invention or a corresponding antisense strand.

Further nucleic acid sequences of the invention are derived from SEQ ID NO:1 and differ therefrom through addition, substitution, insertion or deletion of one or more nucleotides, but still code for polypeptides having the desired profile of properties such as, in particular, the esterase activity of the invention within the abovementioned range of variation in enzymic activity.

The invention also encompasses nucleic acid sequences which comprise so-called silent mutations or are modified, by comparison with a specifically mentioned sequence, in accordance with the codon usage of a specific source or host organism, as well as naturally occurring variants such as, for example, splice variants or allelic variants, thereof. It likewise relates to sequences which are obtainable by conservative nucleotide substitutions (i.e. the relevant amino acid is replaced by an amino acid with the same charge, size, polarity and/or solubility).

The invention also relates to molecules derived from the specifically disclosed nucleic acids through sequence polymorphism. These genetic polymorphisms may exist because of the natural variation between individuals within a population. These natural variations normally result in a variance of from 1 to 5% in the nucleotide sequence of a gene.

The invention additionally encompasses nucleic acid sequences which hybridize with or are complementary to the abovementioned coding sequences. These polynucleotides can be found on screening of genomic or cDNA libraries and, where appropriate, be multiplied therefrom by means of PCR using suitable primers, and then, for example, be isolated with suitable probes. Another possibility is to transform suitable microorganisms with polynucleotides or vectors of the invention, multiply the microorganisms and thus the polynucleotides, and then isolate them. An additional possibility is to synthesize polynucleotides of the invention by chemical routes.

The property of being able to "hybridize" onto polynucleotides means the ability of a polynucleotide or oligonucleotide to bind under stringent conditions to an almost complementary sequence, while there are no nonspecific bindings between noncomplementary partners under these conditions. For this purpose the sequences should be 70-100%, preferably 90-100%, complementary. The property of complementary sequences being able to bind specifically to one another is made use of, for example, in the Northern or Southern blot technique or in PCR or RT-PCR in the case of primer binding. Oligonucleotides with a length of 30 base pairs or more are normally employed for this purpose. Stringent conditions mean, for example, in the Northern blot technique the use of a washing solution at 50-70° C., preferably 60-65° C., for example 0.1×SSC buffer with 0.1% SDS (20×SSC: 3M NaCl, 0.3M Na citrate, pH 7.0) for eluting nonspecifically hybridized cDNA probes or oligonucleotides. In this case, as mentioned above, only nucleic acids with a high degree of complementarity remain bound to one another. The setting up of stringent conditions is known to the skilled worker and is described, for example, in Ausubel et al., Current Protocols in Molecular Biology, John Wiley & Sons, N.Y. (1989), 6.3.1-6.3.6.

The invention also relates to expression cassettes including at least one inventive polynucleotide which is operatively linked to regulatory nucleic acid sequences. Preferably, a promoter sequence is located 5' upstream of the polynucleotide of the invention and facilitates in this way controlled expression of the butynol I esterase. Particularly preferably, a terminator sequence and also, where appropriate, further customary regulatory elements are located 3' downstream of the polynucleotide of the invention, each of them operatively linked to the sequence encoding butynol I esterase. Operative linkage means the sequential arrangement of promoter, coding sequence, terminator and, where appropriate, further regulatory elements such that each of the regulatory elements can fulfil its function before, during or after expression of the coding sequence as intended. Examples of further operatively linkable sequences are targeting sequences and also translation amplifiers, enhancers, polyadenylation signals and the like. Further useful regulatory elements include selectable markers, reporter genes, amplification signals, replication origins and the like.

In addition to the artificial regulatory sequences, the natural regulatory sequence may still be present in front of the actual structural gene. By genetic modification, it is possible, where appropriate, to switch off said natural regulation and to increase or decrease expression of the genes. However, construction of the expression cassette may also be simpler, i.e. no additional regulatory signals are inserted in front of the structural gene, and the natural promoter with its regulation is not removed. Instead, the natural regulatory sequence is mutated such that regulation no longer takes place and gene expression is enhanced or diminished. The nucleic acid sequences may be present in one or more copies in the expression cassette.

Examples of useful promoters are: cos, tac, trp, tet, trp-tet, lpp, lac, lpp-lac, lacIq, T7, T5, T3, gal, trc, ara, SP6, λ-PR or λ-PL promoter which are advantageously used in Gram-negative bacteria; and also the Gram-positive promoters amy and SPO2, the yeast promoters ADC1, MFa, AC, P-60, CYC1, GAPDH or the plant promoters CaMV/35S, SSU, OCS, lib4, usp, STLS1, B33, nos or the ubiquitin promoter or phaseolin promoter. Particular preference is given to using inducible promoters such as, for example, light- and in particular temperature-inducible promoters such as the $P_rP_1$ promoter.

In principle it is possible to use all natural promoters with their regulatory sequences. Moreover, it is also advantageous and possible to use synthetic promoters.

Said regulatory sequences ought to facilitate specific expression of the nucleic acid sequences and protein expression. Depending on the host organism, this can mean, for example, that the gene is expressed or overexpressed only after induction, or that it is expressed and/or overexpressed immediately.

In this context, it is possible for the regulatory sequences or factors to positively influence and thereby increase or decrease expression. Thus, the regulatory elements can be advantageously enhanced at the transcription level by using strong transcription signals such as promoters and/or enhancers. Aside from this, however, it is also possible to enhance translation by, for example, increasing the mRNA stability.

An expression cassette of the invention is produced by fusion of a suitable promoter with a suitable polynucleotide encoding butynol I esterase and also with a terminator or polyadenylation signal. For this, customary recombination and cloning techniques are used, as are described, for example, in T. Maniatis, E. F. Fritsch and J. Sambrook, Molecular Cloning: A Laboratory Manual, Cold Spring Harbor Laboratory, Cold Spring Harbor, N.Y. (1989) and also in T. J. Silhavy, M. L. Berman and L. W. Enquist, Experiments with Gene Fusions, Cold Spring Harbor Laboratory, Cold Spring Harbor, N.Y. (1984) and in Ausubel, F. M. et al., Current Protocols in Molecular Biology, Greene Publishing Assoc. and Wiley Interscience (1987).

The invention also relates to recombinant vectors for transforming eukaryotic and prokaryotic hosts carrying a polynucleotide of the invention or an expression cassette of the invention. Said vectors allow butynol I esterase expression in a suitable host organism. Vectors are well known to the skilled worker and can be found, for example, in "Cloning Vectors" (Pouwels P. H. et al., eds., Elsevier, Amsterdam-New York-Oxford, 1985). Vectors mean, in addition to plasmids, also all other vectors known to the skilled worker such as, for example, phages, viruses such as SV40, CMV, baculovirus and adenovirus, transposons, IS elements, phasmids, cosmids, and linear or circular DNA. These vectors can be replicated autonomously or chromosomally in the host organism.

With the aid of the vectors of the invention it is possible to produce recombinant microorganisms which, for example, have been transformed with at least one vector of the invention and can be employed for producing recombinant esterase. Advantageously, the above-described recombinant expression cassettes of the invention are introduced as part of an expression vector into a suitable host system and expressed. Preference is given here to familiar cloning and transfection methods known to the skilled worker, in order to express said nucleic acids in the particular expression system. Suitable systems are described, for example, in Current Protocols in Molecular Biology, F. Ausubel et al., eds., Wiley Interscience, New York 1997.

Host organisms which are suitable for transformation with vectors of the invention are in principle all organisms facilitating expression of the inventive polynucleotides, of allelic variants, functional equivalents or derivatives thereof. Host organisms mean, for example, bacteria, fungi, yeasts, plant or animal cells. Preferred organisms are bacteria such as those of the genera *Escherichia* such as, for example, *Escherichia coli, Streptomyces, Bacillus* or *Pseudomonas*, eukaryotic microorganisms such as *Saccharomyces cerevisiae, Aspergillus*, higher eukaryotic cells from animals or plants, for example Sf9 or CHO cells. Successfully transformed organisms can be selected through marker genes which are likewise contained in the vector or in the expression cassette. Examples of such marker genes are genes for antibiotics resistance and for enzymes catalyzing a staining reaction causing staining of the transformed cells. Said cells can then be selected by means of automated cell sorting. Organisms which have been successfully transformed with a vector and which carry an appropriate antibiotics resistance gene can be selected on media or substrates containing appropriate antibiotics. Marker proteins presented at the cell surface can be used for selection by means of affinity chromatography.

Thus, the invention also relates to microorganisms carrying a vector of the invention and also to the *Pseudomonas glumae* mutant, Lu 2023, with deposition number DSM 13176, which expresses butynol I esterase endogenously.

The butynol I esterases of the invention in particular catalyze at least one of the following reactions:

a) enantioselective hydrolysis of optically active esters of the formula I $$R^1\text{—COO—}R^2 \qquad (I),$$

in which $R^1$ is a straight-chain or branched, unsubstituted or monosubstituted or polysubstituted $C_1$-$C_{10}$- alkyl, $C_2$-$C_{10}$-alkenyl, $C_2$-$C_{10}$-alkynyl and $R^2$ is a straight-chain or branched, unsubstituted or mono-substituted or polysubstituted $C_1$-$C_{10}$-alkyl, $C_2$-$C_{10}$-alkenyl, $C_2$-$C_{10}$-alkynyl, $C_7$-$C_{15}$-aralkyl or a mononuclear or polynuclear, unsubstituted or monosubstituted or polysubstituted aromatic radical, $R^1$ and/or $R^2$ include at least one asymmetric carbon, where particularly preferably either the carbon from $R^1$ bound to the ester bond carbon or the carbon from $R^2$ bound to the ester bond oxygen is an asymmetric carbon; and b) enantioselective transesterification of an ester of the formula I with an optically active alcohol of the formula II

$$R^2\text{—OH} \quad\quad\quad\quad (II),$$

in which $R^2$ has one of the above meanings and, where appropriate, has at least one asymmetric carbon,
where particularly preferably the carbon carrying the OH group is an asymmetric carbon.

The invention also relates to methods for enantioselective ester hydrolysis using butynol I esterase, in which methods butynol I esterase is contacted with a stereoisomer mixture of an optically active ester of the formula I and the optically active compounds arising from the stereoselective hydrolysis of any of the two stereoisomers and/or the non-hydrolyzed ester enantiomer are obtained from the reaction medium. It is, however, also possible for butynol I esterase to hydrolyze those esters of the formula I which are not optically active.

The invention also relates to methods for enantioselective transesterification, in which methods a stereoisomer mixture of an optically active alcohol of the formula II is contacted with an ester of the formula I in the presence of butynol I esterase, and the unreacted alcohol stereoisomer is obtained from the reaction medium, or a stereoisomer mixture of an optically active ester of the formula I is contacted with an alcohol of the formula II in the presence of butynol I esterase, and a stereoisomer of the optically active alcohol contained in the ester is obtained from the reaction medium. Vinyl esters are preferably used in transesterification as acylating agents for an optically active alcohol. This is advantageous because, after the conversion, the alcohol function of the vinyl ester is no longer available for the reverse reaction due to tautomerisation. Butynol I esterase also catalyses transesterification processes in which neither the ester nor the alcohol is optically active.

Preferred substrates of ester hydrolysis are esters of ethanol, propanol, butanol and, particularly preferably, butynyl esters (butynol esters, esters of 1-methylprop-2-ynol) with carboxylic acids such as, for example, acetic acid, propionic acid, butyric acid, pentanoic acid, hexanoic acid, heptanoic acid, octanoic acid, lactic acid, 2-ethylhexanoic acid, 3-methylbutyric acid, methoxyacetic acid, 2-methylpropionic acid, 2-butenoic acid, 3-chloropropionic acid and 2-methylpentanoic acid. Particular preference is given to butynyl butyrate and butynyl methylbutyrate.

Preferred alcohols in the transesterification are ethanol, propanol and butanol, particularly preferred is butynol.

Preferred esters in the transesterification are vinyl esters such as, for example, vinyl acetate, vinyl propionate and vinyl butyrate.

Reaction media used in the above methods are organic solvents such as, for example, alkanes, ethers, toluene, dioxane, methyl isobutyl ketone, methyl tert-butyl ether (MTBE) and the like. In the ester hydrolysis, mixtures made from the buffer solution used and organic solvents such as, for example, MTBE and heptane or toluene may also be used.

The invention also relates to the optically active alcohols, carboxylic acids or esters prepared by the above methods using butynol I esterase.

Racemate resolution, i.e. enantioselectivity, and reaction rate can be influenced via size and hydrophobicity of the acid moiety. The reaction is preferably carried out at room temperature at from pH 6 to 9, particularly preferably at from pH 7.0 to 7.4. The esterase may be employed in the form of isolated or purified enzyme, as cells of the microorganism expressing the esterase, as culture supernatant, cell lysate or extract of said microorganism, or as immobilized esterase. The reaction products can be isolated from the reaction solution by chemical or physical separation methods known to the skilled worker. Butynol I esterase can be isolated from the reaction mixture by membrane filtration.

It is possible to immobilize the esterase with the aid of polyacrylamide, alginic acid or carrageenans. It is also possible to bind the esterase covalently or by adsorption to suitable carriers by means of known methods. Butynol I esterase is preferably immobilized by lyophilization on kieselguhr or by ammonium sulfate precipitation.

As mentioned above, butynol I esterase is obtainable from *Pseudomonas glumae* Lu 2023. It can, however, also be prepared by means of known peptide synthesis methods.

Furthermore, butynol I esterase is also obtainable from eukaryotic or prokaryotic organisms, if said organisms express butynol I esterase, such as microorganisms carrying a vector of the invention, for example.

Thus, the invention also relates to methods for preparing butynol I esterase, in which methods microorganisms which produce butynol I esterase or a microorganism transformed with a vector of the invention are cultured, butynol I esterase expression is, where appropriate, induced and butynol I esterase is isolated from the culture. The microorganisms can be cultured and fermented using known methods. For example, bacteria may be amplified in TB or LB medium at from 20 to 40° C. and from pH 6 to 9. Suitable culturing conditions are described in detail in, for example, T. Maniatis, E. F. Fritsch and J. Sambrook, Molecular Cloning: A Laboratory Manual, Cold Spring Harbor Laboratory, Cold Spring Harbor, N.Y. (1989).

After culturing, the cells are lysed, and butynol I esterase is obtained from the lysate by protein isolation methods. The cells may be lysed as desired either by high frequency ultrasound, by high pressure as, for example, in a French press, by osmosis, by the action of detergents, lytic enzymes or organic solvents, by homogenizers, preferably glass bead mills, or by a combination of two or more of the stated methods. After centrifugation, proteins and other soluble molecules remain in the supernatant. Precipitation of the DNA using manganese chloride can produce a distinctly less viscous solution. Proteins may be selectively precipitated through salting out by using, for example, ammonium sulfate or potassium phosphate. Precipitation can also occur through pH or temperature change or through organic solvents such as methanol, ethanol or acetone. After salt precipitation, said salts can be removed by dialysis.

Further purification of butynol I esterase can be achieved by using known chromatographic methods such as molecular sieve chromatography (gel filtration), Q-Sepharose chromatography, ion exchange chromatography and hydrophobic chromatography, and also by using other customary methods such as ultrafiltration, crystallization and native gel electrophoresis.

The following nonlimiting examples illustrate the invention in more detail with reference to the attached figures in which:

EXAMPLE 1

Selection of a *Pseudomonas glumae* Mutant Expressing Butynol I Esterase

Starting point of the screening was the lipase-producing strain *Pseudomonas* (Burkholderia) *glumae* Lu 8093. The lipase produced by said strain makes it possible to carry out a number of interesting reactions (Balkenhohl, F. et al., J. prakt. Chem. 339, (1997), 381-384). Lactic esters, methylbutyric esters and phenylacetic esters, however, are not substrates for the lipase and cannot be hydrolyzed by said strain in any other way either.

The hydrolysis products are, however, usable as carbon source. Therefore, mutants of Lu 8093 were sought which are able to hydrolyze said esters and to grow using the hydrolysis products as carbon source. Mutants with novel esterase activity should therefore reveal themselves by growing on said esters.

Selection conditions: Lu 8093 was cultured on medium for 16 h and harvested by centrifugation. The cells were washed twice with saline. $10^6$ cells were plated out onto minimal medium plates containing 0.5 or 1.0 g/l ethyl phenylacetate as the sole carbon source. Initially, however, there was no growth. Only after 4 to 6 days were single colonies recognizable. Their number increased further over the following days.

From the esterase-positive mutants obtained in this way, the mutant Lu 2023 was selected. Surprisingly, the novel esterase activity was also suitable for selective hydrolysis of relatively small organic molecules. As an example, selective hydrolysis was shown for butynol ester.

EXAMPLE 2

Fermentation of *Pseudomonas glumae* Lu 2023

To obtain butynol I esterase, *Pseudomonas glumae* Lu 2023 was cultured on the 14-1 scale and the active biomass was harvested.

In the laboratory, *Pseudomonas glumae* Lu 2023 was streaked onto agar plates with M12 mineral salt medium and 1 g/l EPA and incubated at 28° C. for 36 to 48 hours. It was then possible to store the plates at 4° C. for four weeks.

Fermentation of the strain was carried out in an Infors xxy 14-1 fermenter. For the preculture, 250 ml of medium were inoculated with 2 to 3 Pt loops and incubated at 200 rpm and 28° C. for 24 hours. The main culture was carried out under the following conditions:

Temperature 28° C.
Air feed 7 l/min
Stirring 600 rpm
Fermentation run time about 24 h
Built-in pH and $pO_2$ measurement Medium for Preculture and Main Culture

| | |
|---|---|
| 15 g/l | Springer yeast autolysate 65% |
| 1.6 g/l | magnesium sulfate × 7 water |
| 0.02 g/l | calcium chloride × 2 water |
| 3.5 g/l | potassium dihydrogen phosphate |
| 3.5 g/l | dipotassium hydrogen phosphate |
| 5 g/l | diammonium hydrogen phosphate |
| 6 ml | Pluriol P2000 antifoam |

The above ingredients were dissolved in deionized water and the solution was adjusted to pH 6.5 using 25% strength ammonia solution. 5 ml/l trace element solution and 2 g/l glucose were sterile-filtered separately.

After sterilizing and completing the medium, 0.5 g/l ethyl phenylacetate was introduced into the fermenter. Addition of Pluriol P2000 controlled the foam appearing during fermentation. Fermentation was stopped when the $pO_2$ in the fermenter increased again to above 85%. The fermenter contents were then centrifuged at below 15° C. and about 9000 to 10 000 g, and the clear effluent was discarded. The cell mass was frozen at −16° C.

EXAMPLE 3

Purification of Butynol I Esterase from *Pseudomonas glumae* Lu 2023

*Pseudomonas glumae* (Lu 2023) cells (100 ml, wet weight: 50 g) were lysed in a glass bead mill (100 ml of glass beads, diameter: 0.5 mm) at 4° C. and 3000 rpm. After centrifugation (10 000 rpm, 30 min) and washing the glass beads, the supernatant (300 ml) was subjected to manganese chloride precipitation (pH 7 to 7.5; final concentration: 50 mM). After another centrifugation, the supernatant was adjusted to pH 8.0 and EDTA was added at a concentration of 50 mM. This volume was purified by Q-Sepharose (300 ml) chromatography. After applying the sample, the column was washed with 50 mM Tris/HCl. The fraction of interest was collected and concentrated by ultrafiltration (100 kDa). butynol I esterase was separated from a nonspecific esterase by molecular sieve chromatography (diameter: 5 cm, height: 90 cm; material: S-300). The active fraction obtained was cloudy and was again concentrated. The esterase was obviously membrane-bound. The membrane fraction was then first digested by a protease (trypsin, weight ratio: 1:50 to 1:100). This caused all proteins to disappear from the membrane fraction apart from a few bands in the SDS polyacrylamide gel electrophoresis. The activity was preserved. Said bands were separated from one another by native gel electrophoresis (0.04% SDS), and an activity assay identified the esterase in said native gel. Said esterase was eluted from the gel and then appeared as a clean band in a denaturing SDS polyacrylamide gel electrophoresis.

The protein purified in this way was transferred by blotting onto a PVDF membrane and sequenced, or, after trypsin cleavage, the peptides were separated by reversed phase HPLC and sequenced. Since the amino terminus of the protein was blocked, only tryptic peptides were obtained. The various amino acid sequences showed weak homologies to a muconate cycloisomerase, EC 5.5.1.1, from Acinetobacter iwoffii and *Pseudomonas putida*, and also lactone esterase from *Pseudomonas fluorescens*. The peptide having the sequence AIDAIFAPEPV (SEQ ID NO: 6) showed homology to pectin-esterases (EC 3.1.1.11).

The drawing in FIG. 1 depicts a sequence alignment of an inventive amino acid part sequence with a part sequence of a lactone-specific esterase from *Pseudomonas fluorescens*.

EXAMPLE 4

Immobilization of Butynol I Esterase

Various methods were employed for the immobilization.
1. Butynol I esterase was substantially inactivated by precipitation with acetone in the presence of kieselguhr. 25 mg of protein were mixed with 3.5 g of kieselguhr (Merck), and 1.4 l of acetone (−20° C.) were added for 10 minutes. The loaded support was then removed via a G3 glass suction filter, the filter residue was washed with cold acetone and dried.

2. Butynol I esterase does not bind to Accurel (Akzo).
3. It was possible to immobilize butynol I esterase (2.3 units/g, EPA assay) on kieselguhr by lyophilization. For this, the enzyme solution was mixed with kieselguhr and frozen at −80° C. Subsequently, the solid substance was dried by lyophilization.
4. Butynol I esterase (454 milliunits/g, EPA assay) was immobilized by ammonium sulfate precipitation. For this, the enzyme was precipitated at 80% saturation of ammonium sulfate in the presence of kieselguhr.

EXAMPLE 5

Racemate Resolution Using Butynol I Esterase from *Pseudomonas glumae* Lu 2023

Procedure (Standard Mixture)

100 units of butynol I esterase were reacted with 20 mmol of butynol butyrate (1-methylprop-2-ynyl butyrate) in phosphate buffer (200 ml, 10 mM, pH 7.4) with stirring. The pH was continuously measured and kept at approx. pH 7.4 by adding sodium hydroxide solution. At the times indicated in table 1, samples were taken and extracted twice with methyl tert-butyl ether (MTBE), and the organic phase was analyzed by GC (Chiraldex GTA). Butynol I esterase was removed from the reaction mixture by membrane filtration.

With its concentration increasing, the less preferred ester enantiomer was increasingly converted. After about 45 minutes, this caused a drop in the ee of S-butynol in the reaction mixture. The ee of the product reached its maximum at 84% (83-97.9%) after approx. 30 to 40 minutes. The ee of the substrate increased to over 99% over the course of 90 minutes. The ee (enantiomer excess) is defined as the amount of the preferably converted enantiomer in percent minus the amount of the less preferably converted enantiomer in percent. In most cases, this corresponds to the optical purity. The drop in pH was linear up to 30 minutes. From approx. 100 minutes onward, the pH change was negligible.

After the extraction, the residual esterase activity in the aqueous phase was still approx. 50%.

TABLE 1

| Time | ee of product (S)-butynol | ee of substrate (R)-butynol ester | Ester conversion in % (corr.) |
| --- | --- | --- | --- |
| 0 min | nd | 5.20 | nd |
| 7 min | nd | 10.20 | nd |
| 13 min | 75.50 | 20.40 | 12 |
| 20 min | 81.80 | 29.10 | 16 |
| 26 min | 83.90 | 42.00 | 22 |
| 32 min | 84.60 | 53.70 | 27 |
| 45 min | 84.00 | 78.80 | 36 |
| 70 min | 70.80 | 97.10 | 47 |
| 90 min | 69.60 | 99.10 | 52 |
| 121 min | 63.10 | 99.40 | 56 |
| 150 min | 52.00 | 99.50 | 67 |

Table 1 shows the time-dependent enantiomer excess on conversion butynol butyrate using butynol I esterase. According to the R/S convention by Cahn, Prelog and Ingold, R and S configurations define the two enantiomers of a chiral molecule. The conversion is the proportion of converted ester in the reaction mixture.

EXAMPLE 6

Dependence of The Butynol I Esterase Specificity on Size and Hydrophobicity/charge of the Acid Moiety of the Ester Standard Approach 100 units of butynol I esterase were reacted with 20 mmol of butynol ester in phosphate buffer (200 ml, 10 mM, pH 7.4) with stirring. The pH was continuously measured and kept at pH 7.0 by continuous titration. Samples taken were extracted twice with methyl tert-butyl ether (MTBE), and the organic phase was analyzed by GC (Chiraldex GTA).

Result

The quality of racemate resolution and the reaction rate depended on size and hydrophobicity of the acid moiety. The best substrates for butynol esterase were butynol butyrate and butynol methyl-butyrate. Lipases are inactive with these substrates. This is also true for long-chain esters such as butynyl n-decanoate.

TABLE 2

| Acid component | ee [%] | Conversion [%] | E |
| --- | --- | --- | --- |
| Acetate | 73 (S) | 48 | 12 |
| Butyrate | 95 (S) | 36 | 67 |
| Pentanoate | 74 (S) | 47 | 13 |
| Hexanoate | 66 (S) | 44 | 8 |
| Octanoate | 64 (S) | 43 | 8 |
| 2-Ethylhexanoate | no conversion | | |
| Phenylacetate | 51 (S) | 12 | 3 |
| 3-Phenylpropionate | 73 (S) | 44 | 11 |
| 3-Cyclohexylpropionate | 22 (S) | 18 | 2 |

Table 2 shows the dependence of the enantiomer excess for converting esters using butynol I esterase on the acid moiety of the converted ester.

EXAMPLE 7

Transesterification in Organic Medium Using Butynol I Esterase 10 mmol of rac-butynol and 5 mmol of vinyl butyrate were dissolved in 50 ml of methyl tert-butyl ether (MTBE) and mixed with 9 units of butynol I esterase (3.3 g) supported on kieselguhr, and the mixture was shaken at room temperature for 24 h. After filtration, the solvent was removed and the product mixture was characterized by GC.

At 47% conversion, (R)-butynol (18% ee) and the butyrate of (S)-butynol (45% ee) remained.

In methyl isobutyl ketone, (R)-butynol with 16% ee and the butyrate of (S)-butynol with 52% ee were obtained at 43% conversion.

Table 3 shows the dependence of the enantiomer excess for converting esters using butynol I esterase on the acid moiety of the converted ester.

TABLE 3

| Mixture No. | Substrate | pH | Temp. [° C.] | Buffer system sol. [mmol/l] | Additives | ee[1] |
| --- | --- | --- | --- | --- | --- | --- |
| 8 | Butynyl n-decanoate | 7.0 | RT | Phosphate 10 | none | 54.37 |
| 14 | Butynyl n-pentanoate | 7.0 | RT | Phosphate 10 | none | 80.40 |

TABLE 3-continued

| Mixture No. | Substrate | pH | Temp. [°C.] | Buffer system sol. [mmol/l] | Additives | ee[1] |
|---|---|---|---|---|---|---|
| 15 | Butynyl 2-ethylhexanoate | 7.0 | RT | Phosphate 10 | none | 81.77 |
| 16 | Butynyl butyrate | 7.0 | RT | Phosphate 10 | none | 83.90 |
| 17 | Butynyl butyrate | 7.0 | RT | Phosphate 10 | 0.5% Triton | 80.83 |
| 18 | Butynyl n-hexanoate | 7.0 | RT | Phosphate 10 | 0.5% Triton | 78.63 |
| 19 | Butynyl n-octanoate | 7.0 | RT | Phosphate 10 | 0.5% Triton | 74.70 |
| 20 | Butynyl butyrate | 7.0 | RT | Phosphate 10 | 10% n-Propanol | 87.47 |
| 21 | Butynyl butyrate | 7.0 | RT | Phosphate 10 | 1 M NaCl | 85.70 |
| 23 | Butynyl n-pentanoate | 7.0 | RT | Phosphate 10 | 0.5% Triton | 84.40 |
| 24 | Butynyl butyrate | 6.0 | RT | Phosphate 10 | none | 85.37 |
| 25 | Butynyl butyrate | 8.0 | RT | Tris 10 | none | 85.33 |
| 26 | Butynyl butyrate | 7.0 | 10 | Phosphate 10 | none | 85.90 |
| 27 | Butynyl butyrate | 7.0 | 37 | Phosphate 10 | none | 75.67 |
| 28 | Butynyl 3-methylbutyrate | 7.0 | RT | Phosphate 10 | none | 90.50 |
| 29 | Butynyl methoxyacetate | 7.0 | RT | Phosphate 10 | none | 76.33 |
| 31 | Butynyl butyrate | 7.0 | RT | Phosphate 10 | none | 85.00 |
| 32 | Butynyl butyrate | 7.0 | RT | Phosphate 10 | 2-phase-system | 84.93 |
| 33 | Butynyl 3-methylbutyrate | 7.0 | RT | Phosphate 10 | 2-phase system | 92.70 |
| 34 | Butynyl 2-methylpropionate | 7.0 | RT | Phosphate 10 | none | 89.17 |
| 35 | Butynyl 2-butenoate | 7.0 | RT | Phosphate 10 | none | 76.03 |
| 36 | Butynyl 3-chloropropionate | 7.0 | RT | Phosphate 10 | none | 71.13 |
| 40 | Butynyl 2-methylpentanoate | 7.0 | RT | Phosphate 10 | none | 85.93 |

[1] Averages of the 3 best values for ee of S-butynol

We claim:

1. An isolated protein comprising an amino acid sequence having:
   SEQ ID NO.: 7; or,
   an amino acid sequence having at least 95% homology with SEQ ID NO.: 7, wherein said isolated protein has butynol I esterase activity.

2. The isolated protein of claim 1, comprising an amino acid sequence having SEQ ID NO.: 2.

3. The isolated protein of claim 1, wherein the amino acid sequence having at least 95% homology with SEQ ID NO: 7 comprises at least 10 successive amino acid residues according to SEQ ID NO.: 3, 4, 5, or 6.

4. The isolated protein of claim 1, comprising a polypeptide chain having a molecular weight of about 41,300 Da as determined by SDS gel electrophoresis.

5. The isolated protein of claim 1, wherein said protein is obtained from *Pseudomonas glumae* Lu 2023 with deposition number DSM 13176.

6. The isolated protein of claim 1, wherein said protein catalyzes at least one of the following reactions:
   a) enantioselective hydrolysis of optically active esters of the formula(I), $$R^1\text{—COO—}R^2 \quad (I),$$

in which
   $R^1$ is a straight-chain or branched, unsubstituted or monosubstituted or polysubstituted $C_1$-$C_{10}$-alkyl, $C_2$-$C_{10}$-alkenyl, $C_2$-$C_{10}$-alkynyl and
   $R^2$ is a straight-chain or branched, unsubstituted or monosubstituted or polysubstituted $C_1$-$C_{10}$-alkyl, $C_2$-$C_{10}$-alkenyl, $C_2$-$C_{10}$-alkynyl, $C_7$-$C_{15}$-aralkyl or a mononuclear or polynuclear, unsubstituted or monosubstituted or polysubstituted aromatic radical,
   $R^1$ and/or $R^2$ include at least one asymmetric carbon; and
   b) enantioselective transesterification of an ester of the formula I with an optically active alcohol of the formula II $$R^2\text{—OH} \quad (II),$$

in which
   $R^2$ is a straight-chain or branched, unsubstituted or monosubstituted or polysubstituted $C_1$-$C_{10}$-alkyl, $C_2$-$C_{10}$-alkenyl, $C_2$-$C_{10}$-alkynyl, $C_7$-$C_{15}$-aralkyl or a mononuclear or polynuclear, unsubstituted or monosubstituted or polysubstituted aromatic radical and, optionally, has at least one asymmetric carbon.

7. A method for preparing an isolated protein comprising an amino acid sequence having one of:
   SEQ ID NO.: 7; or,
   an amino acid sequence having at least 95% homology with SEQ ID NO.: 7, said isolated protein has butynol I esterase activity, the method comprising:
   isolating the protein from a culture of *Pseudomonas glumae* which produces the protein endogenously or a microorganism transformed with a vector including a polynucleotide which codes for the isolated protein.

8. The isolated protein of claim 1 obtained by:
   isolating the protein from a culture of *Pseudomonas glumae* which produces the protein endogenously or a microorganism transformed with a vector, wherein the vector includes a polynucleotide which codes for the isolated protein of claim 1.

9. An isolated protein comprising an amino acid sequence having SEQ ID NO: 2 or, an amino acid sequence having at least 95% homology with SEQ ID NO.: 2, wherein said isolated protein has butynol I esterase activity.

10. The isolated protein of claim 9, comprising an amino acid sequence having SEQ ID NO.: 2.

11. The isolated protein of claim 9, wherein the amino acid sequence having at least 95% homology with SEQ ID NO: 2 comprises at least 10 successive amino acid residues according to SEQ ID NO.: 3, 4, 5, or 6.

12. The isolated protein of claim 9, comprising a polypeptide chain having a molecular weight of about 41,300 Da as determined by SDS gel electrophoresis.

13. The isolated protein of claim 9, wherein said protein is obtained from *Pseudomonas glumae* Lu 2023 with deposition number DSM 13176.

14. The isolated protein of claim 9, wherein said protein catalyzes at least one of the following reactions:
   a) enantioselective hydrolysis of optically active esters of the formula(I), $$R^1\text{—COO—}R^2 \quad (I),$$

in which
   $R^1$ is a straight-chain or branched, unsubstituted or monosubstituted or polysubstituted $C_1$-$C_{10}$-alkyl, $C_2$-$C_{10}$-alkenyl, $C_2$-$C_{10}$-alkynyl and $R^2$ is a straight-chain or branched, unsubstituted or monosubstituted or polysubstituted $C_1$-$C_{10}$-alkyl, $C_2$-$C_{10}$-alkenyl, $C_2$-$C_{10}$-alkynyl, $C_7$-$C_{15}$-aralkyl or a mononuclear or polynuclear, unsubstituted or monosubstituted or polysubstituted aromatic radical,
   $R^1$ and/or $R^2$ include at least one asymmetric carbon; and
   b) enantioselective transesterification of an ester of the formula I with an optically active alcohol of the formula II $$R^2\text{—OH} \quad (II),$$

in which
   $R^2$ is a straight-chain or branched, unsubstituted or monosubstituted or polysubstituted $C_1$-$C_{10}$-alkyl, $C_2$-$C_{10}$-alkenyl, $C_2$-$C_{10}$-alkynyl, $C_7$-$C_{15}$-aralkyl or a mononuclear or polynuclear, unsubstituted or monosubstituted or polysubstituted aromatic radical and, optionally, has at least one asymmetric carbon.

15. A method for preparing an isolated protein comprising an amino acid sequence having one of:
SEQ ID NO.: 2; or,
an amino acid sequence having at least 95% homology with SEQ ID NO.: 2, said isolated protein has butynol I esterase activity, the method comprising:
isolating the protein from a culture of a microorganism which produces the protein endogenously or a microorganism transformed with a vector including a polynucleotide which codes for the isolated protein.

16. The isolated protein of claim 9 obtained by:
isolating the protein from a culture of a microorganism which produces the protein endogenously or a microorganism transformed with a vector, wherein the vector includes a polynucleotide which codes for the isolated protein of claim 1.

* * * * *

SEQUENCE LISTING

<160> NUMBER OF SEQ ID NOS: 6

<210> SEQ ID NO 1
<211> LENGTH: 1530
<212> TYPE: DNA
<213> ORGANISM: Pseudomonas glumae LU 2023
<220> FEATURE:
<221> NAME/KEY: CDS
<222> LOCATION: (1)..(1530)

<400> SEQUENCE: 1

```
atg atc gtc caa ctg atc gcc atc gtg gtc gcc ctc tac gcc gtg ctg    48
Met Ile Val Gln Leu Ile Ala Ile Val Val Ala Leu Tyr Ala Val Leu
 1               5                  10                  15 ttc gcg ttc acg ctg ttc acc gcg cat cag gtg cgc cgc ttt ccg         96
Phe Ala Phe Thr Leu Phe Thr Ala His Gln Val Arg Arg Phe Pro
            20                  25                  30 ccc gag ggc aag ttc gtc gag atc gac ggc gac cgc ctg cat tat gtc   144
Pro Glu Gly Lys Phe Val Glu Ile Asp Gly Asp Arg Leu His Tyr Val
        35                  40                  45 gac tac ggc agc ggg ccg ccg atc gtg atg gtg cat ggc ctg tgc ggg   192
Asp Tyr Gly Ser Gly Pro Pro Ile Val Met Val His Gly Leu Cys Gly
    50                  55                  60 cag ctg ctg aac ttc gcc tac ctc gat ctg gcg cgg ctc gcg cag tcg   240
Gln Leu Leu Asn Phe Ala Tyr Leu Asp Leu Ala Arg Leu Ala Gln Ser
65                  70                  75                  80 cat cgc gtg atc ctc gtc gat cgg gcc ggc tcg gga cgc tcg acg cgc   288
His Arg Val Ile Leu Val Asp Arg Ala Gly Ser Gly Arg Ser Thr Arg
                85                  90                  95 ggc ccc gcc tcg cgc gcg aac gtc tat gcg cag gcg cgc ggc atc gcc   336
Gly Pro Ala Ser Arg Ala Asn Val Tyr Ala Gln Ala Arg Gly Ile Ala
            100                 105                 110 cgc ttc atc gag acg ctc ggc ctg gag cgg ccg gtg ctg gtg ggc cat   384
Arg Phe Ile Glu Thr Leu Gly Leu Glu Arg Pro Val Leu Val Gly His
        115                 120                 125 tcg ctc ggc ggc gcg atc gcg ctc gcg gtc ggc ctg gac tac ccc gag   432
```

```
                Ser Leu Gly Gly Ala Ile Ala Leu Ala Val Gly Leu Asp Tyr Pro Glu
                    130                 135                 140 cgc gtg agc cgc atc gcg ctg atc gcg ccg ctc acg cac acc gag acc          480
Arg Val Ser Arg Ile Ala Leu Ile Ala Pro Leu Thr His Thr Glu Thr
145                 150                 155                 160 gag ccg ccc aag gcg ttc cgc ggg ctc gcg ctg cgc ccg gcg gcg ctg          528
Glu Pro Pro Lys Ala Phe Arg Gly Leu Ala Leu Arg Pro Ala Ala Leu
                165                 170                 175 cgc cgc ttc gcg tcg ctg acg atg ggc atc ccg atc atg att ctg caa          576
Arg Arg Phe Ala Ser Leu Thr Met Gly Ile Pro Ile Met Ile Leu Gln
            180                 185                 190 agc cgc aag gcg atc gac gcg atc ttc gcg ccg gag ccg gtg ccg cgc          624
Ser Arg Lys Ala Ile Asp Ala Ile Phe Ala Pro Glu Pro Val Pro Arg
        195                 200                 205 gat ttc ccg ctg aag ggc ggc ggc atg atg ggg ctg cgg ccc gag gcg          672
Asp Phe Pro Leu Lys Gly Gly Gly Met Met Gly Leu Arg Pro Glu Ala
    210                 215                 220 ttc tac gcg gcg tcg tcg gac ctg gtc gcc gcg ccc gag gac ctg ccc          720
Phe Tyr Ala Ala Ser Ser Asp Leu Val Ala Ala Pro Glu Asp Leu Pro
225                 230                 235                 240 gac atg gag cgc cgc tac ccg acg ctg ggc gtg ccg gtc agc atg ctg          768
Asp Met Glu Arg Arg Tyr Pro Thr Leu Gly Val Pro Val Ser Met Leu
                245                 250                 255 tac ggg cgc cag gac gcg atc ctc gat ttc cac aag cat ggc gag ggg          816
Tyr Gly Arg Gln Asp Ala Ile Leu Asp Phe His Lys His Gly Glu Gly
                260                 265                 270 ctc aag cgc aag ctc gac ggc gtc gag ctg agc gcc gtc gag ggc ggg          864
Leu Lys Arg Lys Leu Asp Gly Val Glu Leu Ser Ala Val Glu Gly Gly
            275                 280                 285 cac atg ctg ccc gtg acg cag ccg gcc gcc acc acc gac tgg ctc ctc          912
His Met Leu Pro Val Thr Gln Pro Ala Ala Thr Thr Asp Trp Leu Leu
        290                 295                 300 gcg gtg gcc gcg gcg gcg aac gcg gcg gcg cag cac gat gcg gcg cgg          960
Ala Val Ala Ala Ala Ala Asn Ala Ala Ala Gln His Asp Ala Ala Arg
305                 310                 315                 320 ccg gat ccg gca ccg tcc gag gtc acg cag gcc ggc gcg ctg cag cat         1008
Pro Asp Pro Ala Pro Ser Glu Val Thr Gln Ala Gly Ala Leu Gln His
                325                 330                 335 ctg aag gtc ggc gac aac gtg ctg atc ggc aag aag ccc acc ggc acg         1056
Leu Lys Val Gly Asp Asn Val Leu Ile Gly Lys Lys Pro Thr Gly Thr
                340                 345                 350 ctg gtg gcc gac aac ctg ctg ccg ggc aag acc ctg tgg ctg ctg tcg         1104
Leu Val Ala Asp Asn Leu Leu Pro Gly Lys Thr Leu Trp Leu Leu Ser
            355                 360                 365 acc ggc acg ggt ctc gcg ccg ttc atg tcg atc atc cgc gat ccg gac         1152
Thr Gly Thr Gly Leu Ala Pro Phe Met Ser Ile Ile Arg Asp Pro Asp
        370                 375                 380 atc tac gaa cgc tac gag aag gtg gtg ctc acg cac acc tgc cgc ctg         1200
Ile Tyr Glu Arg Tyr Glu Lys Val Val Leu Thr His Thr Cys Arg Leu
385                 390                 395                 400 aag ggc gag ctc gcg tac atg gac ttc atc aag cac gac ctg ccg ggc         1248
Lys Gly Glu Leu Ala Tyr Met Asp Phe Ile Lys His Asp Leu Pro Gly
                405                 410                 415 cat gag tac ctc ggc gac atc atc aag gaa aag ctg atc tac tac ccg         1296
His Glu Tyr Leu Gly Asp Ile Ile Lys Glu Lys Leu Ile Tyr Tyr Pro
                420                 425                 430 acc gtc acg cgc gaa gcg ttc gac aac gag ggg cgg atc acc gac ctg         1344
Thr Val Thr Arg Glu Ala Phe Asp Asn Glu Gly Arg Ile Thr Asp Leu
            435                 440                 445
```

| | | |
|---|---|---|
| atc tcg acg ggc aag ctg ttc acc gat ctc gac gtc ccg ccg ttc tcg<br>Ile Ser Thr Gly Lys Leu Phe Thr Asp Leu Asp Val Pro Pro Phe Ser<br>450                            455                        460 | | 1392 |
| ccc gag aac gac cgc gtg atg ctg tgc ggc agc acc gcg atg ctg aag<br>Pro Glu Asn Asp Arg Val Met Leu Cys Gly Ser Thr Ala Met Leu Lys<br>465                        470                        475                    480 | | 1440 |
| gac acc acc gac ctg ctc aag cag gcc ggc ctc gtc gaa ggc aag aac<br>Asp Thr Thr Asp Leu Leu Lys Gln Ala Gly Leu Val Glu Gly Lys Asn<br>                        485                        490                    495 | | 1488 |
| agc gcg ccg ggc cac tat gtg atc gaa cgc gca ttt gtc gac<br>Ser Ala Pro Gly His Tyr Val Ile Glu Arg Ala Phe Val Asp<br>            500                    505                    510 | | 1530 |

<210> SEQ ID NO 2
<211> LENGTH: 510
<212> TYPE: PRT
<213> ORGANISM: Pseudomonas glumae LU 2023

<400> SEQUENCE: 2

Met Ile Val Gln Leu Ile Ala Ile Val Ala Leu Tyr Ala Val Leu
 1               5                  10                  15

Phe Ala Phe Thr Leu Phe Thr Ala His Gln Val Arg Arg Phe Pro
                20                  25                  30

Pro Glu Gly Lys Phe Val Glu Ile Asp Gly Asp Arg Leu His Tyr Val
            35                  40                  45

Asp Tyr Gly Ser Gly Pro Pro Ile Val Met Val His Gly Leu Cys Gly
        50                  55                  60

Gln Leu Leu Asn Phe Ala Tyr Leu Asp Leu Ala Arg Leu Ala Gln Ser
65                  70                  75                  80

His Arg Val Ile Leu Val Asp Arg Ala Gly Ser Gly Arg Ser Thr Arg
                85                  90                  95

Gly Pro Ala Ser Arg Ala Asn Val Tyr Ala Gln Ala Arg Gly Ile Ala
            100                 105                 110

Arg Phe Ile Glu Thr Leu Gly Leu Glu Arg Pro Val Leu Val Gly His
        115                 120                 125

Ser Leu Gly Gly Ala Ile Ala Leu Ala Val Gly Leu Asp Tyr Pro Glu
    130                 135                 140

Arg Val Ser Arg Ile Ala Leu Ile Ala Pro Leu Thr His Thr Glu Thr
145                 150                 155                 160

Glu Pro Pro Lys Ala Phe Arg Gly Leu Ala Leu Arg Pro Ala Ala Leu
                165                 170                 175

Arg Arg Phe Ala Ser Leu Thr Met Gly Ile Pro Ile Met Ile Leu Gln
            180                 185                 190

Ser Arg Lys Ala Ile Asp Ala Ile Phe Ala Pro Glu Pro Val Pro Arg
        195                 200                 205

Asp Phe Pro Leu Lys Gly Gly Met Met Gly Leu Arg Pro Glu Ala
    210                 215                 220

Phe Tyr Ala Ala Ser Ser Asp Leu Val Ala Ala Pro Glu Asp Leu Pro
225                 230                 235                 240

Asp Met Glu Arg Arg Tyr Pro Thr Leu Gly Val Pro Val Ser Met Leu
                245                 250                 255

Tyr Gly Arg Gln Asp Ala Ile Leu Asp Phe His Lys His Gly Glu Gly
            260                 265                 270

Leu Lys Arg Lys Leu Asp Gly Val Glu Leu Ser Ala Val Glu Gly Gly
        275                 280                 285

His Met Leu Pro Val Thr Gln Pro Ala Ala Thr Thr Asp Trp Leu Leu

```
                290                 295                 300
Ala Val Ala Ala Ala Asn Ala Ala Gln His Asp Ala Ala Arg
305                 310                 315                 320

Pro Asp Pro Ala Pro Ser Glu Val Thr Gln Ala Gly Ala Leu Gln His
                325                 330                 335

Leu Lys Val Gly Asp Asn Val Leu Ile Gly Lys Lys Pro Thr Gly Thr
                340                 345                 350

Leu Val Ala Asp Asn Leu Leu Pro Gly Lys Thr Leu Trp Leu Leu Ser
                355                 360                 365

Thr Gly Thr Gly Leu Ala Pro Phe Met Ser Ile Ile Arg Asp Pro Asp
370                 375                 380

Ile Tyr Glu Arg Tyr Glu Lys Val Val Leu Thr His Thr Cys Arg Leu
385                 390                 395                 400

Lys Gly Glu Leu Ala Tyr Met Asp Phe Ile Lys His Asp Leu Pro Gly
                405                 410                 415

His Glu Tyr Leu Gly Asp Ile Ile Lys Glu Lys Leu Ile Tyr Tyr Pro
                420                 425                 430

Thr Val Thr Arg Glu Ala Phe Asp Asn Glu Gly Arg Ile Thr Asp Leu
                435                 440                 445

Ile Ser Thr Gly Lys Leu Phe Thr Asp Leu Asp Val Pro Pro Phe Ser
450                 455                 460

Pro Glu Asn Asp Arg Val Met Leu Cys Gly Ser Thr Ala Met Leu Lys
465                 470                 475                 480

Asp Thr Thr Asp Leu Leu Lys Gln Ala Gly Leu Val Glu Gly Lys Asn
                485                 490                 495

Ser Ala Pro Gly His Tyr Val Ile Glu Arg Ala Phe Val Asp
                500                 505                 510
```

<210> SEQ ID NO 3
<211> LENGTH: 32
<212> TYPE: PRT
<213> ORGANISM: Pseudomonas glumae Lu2023

<400> SEQUENCE: 3

```
Phe Ile Glu Thr Leu Gly Leu Glu Arg Pro Val Leu Val Gly His Ser
1               5                   10                  15

Leu Gly Gly Ala Ile Ala Leu Ala Val Gly Leu Asp Tyr Pro Glu Arg
                20                  25                  30
```

<210> SEQ ID NO 4
<211> LENGTH: 14
<212> TYPE: PRT
<213> ORGANISM: Pseudomonas glumae Lu2023

<400> SEQUENCE: 4

```
Ile Ala Leu Ile Ala Pro Leu Thr His Thr Glu Thr Glu Pro
1               5                   10
```

<210> SEQ ID NO 5
<211> LENGTH: 20
<212> TYPE: PRT
<213> ORGANISM: Pseudomonas glumae Lu2023

<400> SEQUENCE: 5

```
Gly Gly Gly Met Met Gly Leu Arg Pro Glu Ala Phe Tyr Ala Ala Ser
1               5                   10                  15

Ser Asp Leu Val
                20
```

```
<210> SEQ ID NO 6
<211> LENGTH: 11
<212> TYPE: PRT
<213> ORGANISM: Pseudomonas glumae Lu2023

<400> SEQUENCE: 6

Ala Ile Asp Ala Ile Phe Ala Pro Glu Pro Val
 1               5                  10
```